United States Patent [19]

Dattagupta et al.

[11] Patent Number: 4,713,326

[45] Date of Patent: * Dec. 15, 1987

[54] COUPLING OF NUCLEIC ACIDS TO SOLID SUPPORT BY PHOTOCHEMICAL METHODS

[75] Inventors: Nanibhushan Dattagupta, New Haven; Donald M. Crothers, Northford, both of Conn.

[73] Assignee: Molecular Diagnostics, Inc., West Haven, Conn.

[ * ] Notice: The portion of the term of this patent subsequent to Sep. 17, 2002 has been disclaimed.

[21] Appl. No.: 611,667

[22] Filed: May 18, 1984

Related U.S. Application Data

[63] Continuation-in-part of Ser. No. 511,064, Jul. 5, 1983, Pat. No. 4,542,102.

[51] Int. Cl.[4] .............................................. G01N 33/50
[52] U.S. Cl. .......................................... 435/6; 422/57; 436/63; 436/94; 436/501; 935/78
[58] Field of Search ............... 435/6; 422/57; 436/63, 436/94, 501; 935/78

[56] References Cited

U.S. PATENT DOCUMENTS

| | | | |
|---|---|---|---|
| 4,542,102 | 9/1985 | Dattagupta | 435/6 |
| 4,582,789 | 4/1986 | Sheldon | 435/6 |
| 4,592,998 | 6/1986 | Avrameas | 435/6 X |

FOREIGN PATENT DOCUMENTS 131830 1/1985 European Pat. Off. .

Primary Examiner—Sidney Marantz
Attorney, Agent, or Firm—Sprung Horn Kramer & Woods

[57] ABSTRACT

A solid support capable of binding a nucleic acid thereto upon suitable irradiation, comprising (a) a solid substrate, (b) a photochemically reactive intercalator compound or other nucleic acid-binding ligands, and (c) divalent radical chemically linking the substrate and the ligand (b). Specifically, a hydroxy group-containing solid substrate such as nitrocellulose paper is linked via a bifunctional reagent such as cyanogen bromide or 1,4-butanedioldiglycidyl ether to an amino-substituted angelicin or psoralen or ethidium bromide which in turn is photochemically linked to a nucleic acid. The resulting immobilized nucleic acid probe is capable of hybridizing with complementary nucleic acid fragments and is thereby useful in diagnostic assays.

12 Claims, No Drawings

COUPLING OF NUCLEIC ACIDS TO SOLID SUPPORT BY PHOTOCHEMICAL METHODS

This is a continuation-in-part of Application Ser. No. 511,064, filed July 5, 1983, U.S. Pat. No. 4,542,102.

The present invention relates to a novel way of joining a nucleic acid to a solid substrate so as to provide a solid probe suitable for use in various tests, particularly hybridization assays for the determination of specific polynucleotide sequences.

In DNA-DNA hybridization and DNA-RNA hybridization assays, one of the complementary nucleic acid chains is commonly coupled to a solid support. This helps to reduce the background and can be used to separate or isolate the corresponding nucleic acid. The methods of attachment of DNA to a solid support have involved (1) non-specific physical adsorption of a single-stranded DNA to nitrocellulose papers, and (2) covalent attachment via diazo coupling. Both methods are specific for single-stranded DNA. These covalent reactions are non-specific and several sites are coupled. These cause ineffective hybridization and loss of perfect fidelity. Several points of attachment per chain reduces the flexibility of the DNA and reduces the rate of hybridization. Moreover, the lifetime of such an adduct is not very long. The DNA comes off easily and it is difficult to quantify the amount on the solid support, without the use of radioactivity. The use of DNA probes for diagnostic purposes demands an effective method of tagging the DNA to a phase which can be separated easily from the rest of the nucleic acids.

Application Ser. No. 511,063, filed on July 5, 1983, U.S. Pat. No. 4,542,102 to Dattagupta, Rae and Crothers discloses various tests for nucleic acids, e.g., DNA of individuals being tested for sickle cell anemia. The test involves a soluble labelled probe and a probe fixed to a solid support. The probe can be fixed to the support chemically as by a bifunctional reagent which at one end reacts with the support, e.g., a hydroxyl group of a cellulose molecule, and at the other end reacts with the DNA. This is quite satisfactory for many purposes but in some instances there may be too much bonding between the substrate and DNA, impairing the sensitivity of the DNA in the test.

It is accordingly an object of the present invention to provide a way of binding a nucleic acid to a solid substrate easily and without impairing the sensitivity of the DNA in the test.

These and other objects and advantages are realized in accordance with the present invention wherein there is provided a solid support capable of binding a nucleic acid thereto upon suitable irradiation, comprising (a) a solid substrate, (b) a photochemically reactive nucleic acid-binding ligand, and (c) a divalent radical chemically linking the substrate and the nucleic acid-binding ligand.

The specific coupling reagents employed are functionalized, photochemically reactive nucleic acid-binding ligands, e.g., intercalator compounds such as amino-substituted furocoumarins, e.g., amino-methyl-dimethyl-angelicin and amino-methyl-trimethyl-psoralen, and aminophenanthridium halides as well as closely related chemical derivatives thereof, and non-intercalator compounds such as netropsin, distamycin, Hoechst 33258 and bis-benzimidazole. Upon photoactivation these reagents will chemically link with nucleic acids. These reagents have a functionalized site other than the nucleic acid-reactive site and, by such other site, they are joined to a solid substrate, thereby in turn joining the nucleic acid to such substrate with a minimum impairment of the nucleic acid function.

Apparently functionalized and photochemically reactive forms of a wide variety of intercalating agents can be used as the coupling reagent as exemplified in the following table:

| Intercalator Classes and Representative Compounds | Literature References |
|---|---|
| A. Acridine dyes | Lerman, J. Mol. Biol. 3:18(1961); Bloomfield et al, "Physical Chemistry of Nucleic Acids", Chapter 7, pp. 429–476, Harper and Rowe, NY(1974) |
| proflavin, acridine orange, quinacrine, acriflavine | Miller et al, Biopolymers 19:2091(1980) |
| B. Phenanthridines | Bloomfield et al, supra; Miller et al, supra |
| ethidium coralyne ellipticine, ellipticine cation and derivatives | Wilson et al, J. Med. Chem. 19:1261(1976) Festy et al, FEBS Letters 17:321(1971); Kohn et al, Cancer Res. 35:71(1976); LePecq et al, PNAS (USA)71: 5078(1974); Pelaprat et al, J. Med. Chem. 23:1330(1980) |
| C. Phenazines 5-methylphenazine cation | Bloomfield et al, supra |
| D. Phenothiazines chlopramazine | ibid |
| E. Quinolines chloroquine quinine | ibid |
| F. Aflatoxin | ibid |
| G. Polycyclic hydrocarbons and their oxirane derivatives | ibid |
| 3,4-benzpyrene, benzpyrene diol epoxide, 1-pyrenyl-oxirane | Yang et al, Biochem. Biophys. Res. Comm. 82:929(1978) |
| benzanthracene-5,6-oxide | Amea et al, Science 176:47(1972) |
| H. Actinomycins actinomycin D | Bloomfield et al, supra |
| I. Anthracyclinones β-rhodomycin A daunamycin | ibid |
| J. Thiaxanthenones miracil D | ibid |
| K. Anthramycin | ibid |
| L. Mitomycin | Ogawa et al, Nucl. Acids Res., Spec. Publ. 3:79(1977); Akhtar et al, Can. J. Chem. 53:2891(1975) |
| M. Platinum Complexes | Lippard, Accts. Chem. Res. 11:211(1978) |
| N. Polyintercalators echinomycin | Waring et al, Nature 252:653(1974); Wakelin, Biochem. J. 157:721(1976) |
| quinomycin triostin BBM928A tandem | Lee et al, Biochem. J. 173:115(1978); Huang et al, Biochem. 19: 5537(1980): Viswamitra et al, Nature 289: 817(1981) |
| diacridines | LePecq et al, PNAS (USA)72:2915(1975): Carrellakis et al, Biochim. Biophys. Acta 418:277(1976); |

-continued

| Intercalator Classes and Representative Compounds | Literature References |
|---|---|
| | Wakelin et al, Biochem 17:5057(1978); Wakelin et al, FEBS Lett. 104:261(1979); Capelle et al, Biochem. 18:3354(1979); Wright et al, Biochem. 19:5825(1980); Bernier et al, Biochem. J. 199:479(1981); King et al, Biochem. 21:4982(1982) |
| ethidium dimer | Gaugain et al, Biochem. 17:5078(1978); Kuhlman et al, Nucl. Acids Res. 5:2629(1978); Marlcovits et al, Anal. Biochem. 94:259(1979): Dervan et al, JACS 100:1968(1978); ibid 101:3664(1979). |
| ellipticene dimers and analogs | Debarre et al, Compt. Rend. Ser. D. 284: 81(1977); Pelaprat et al, J. Med. Chem. 23:1336(1980) |
| heterodimers | Cain et al, J. Med. Chem. 21:658(1978); Gaugain et al, Biochem. 17:5078(1978) |
| trimers | Hansen et al, JCS Chem. Comm. 162(1983); Atnell et al, JACS 105:2913(1983) |
| O. Norphillin A | Loun et al, JACS 104: 3213(1982) |
| P. Fluorenes and fluorenones fluorenodiamines | Bloomfield et al, supra Witkowski et al, Wiss. Beitr.-Martin-Luther-Univ. Halle Wittenberg, 11(1981) |
| Q. Furocoumarins angelicin | Venema et al, MGG, Mol. Gen. Genet. 179;1(980) |
| 4,5'-dimethylangelicin | Vedaldi et al, Chem.-Biol. Interact. 36: 275(1981) |
| psoralen | Marciani et al, Z. Naturforsch B 27(2): 196(1972) |
| 8-methoxypsoralen | Belognzov et al, Mutat. Res. 84:11(1981); Scott et al, Photochem. Photobiol. 34:63(1981) |
| 5-aminomethyl-8-methoxypsoralen | Hansen et al, Tet. Lett. 22:1847(1981) |
| 4,5,8-trimethylpsoralen | Ben-Hur et al, Biochim. Biophys. Acta 331:181(1973) |
| 4'-aminomethyl-4,5,8-trimethylpsoralen | Issacs et al, Biochem. 16:1058(1977) |
| xanthotoxin | Beaumont et al, Biochim. Biophys. Acta 608:1829(1980) |
| R. Benzodipyrones | Murx et al, J. Het. Chem. 12:417(1975); Horter et al, Photochem. Photobiol. 20: 407(1974) |
| S. Monostral Fast Blue | Juarranz et al, Acta Histochem. 70:130(1982) |

Angelicin, more accurately 4'-aminomethyl-4,5'-dimethylangelicin, has the structural formula

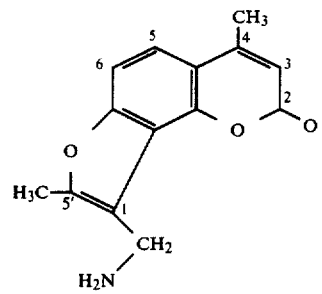

(see Dall'Acquz et al, Photochemistry and Photobiology, Vol. 37, No. 4, pp. 373-379, 1983.)

Psoralen, more accurately 4'-aminomethyl-4,5',8-trimethyl-psoralen (AMT), has the structural formula

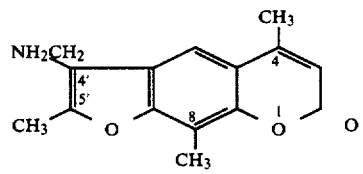

(Cadet et al, Photochemistry and Photobiology, Vol. 37, No. 4, pp. 363-371, 1983.)

Methidium chloride, for example, has the formula

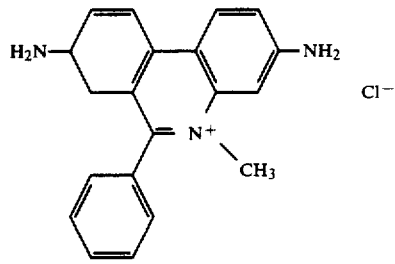

(see Graves et al, Biochemistry, 1981, Vol. 20 pp. 1887-1892.) Its mono- and di-azide analogues, shown below, are comparably reactive:

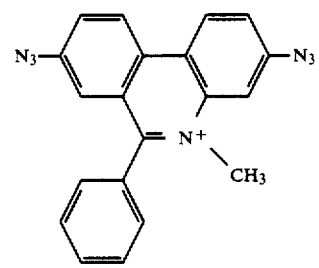

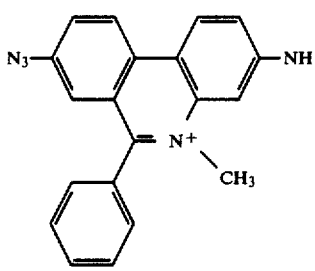

as are the ethyl counterparts and the 4-(3-aminopropyl-N-carbamoyl) derivative of the phenyl side chain (methidium propylamine).

The solid substrate can be any solid which has reactive groups which could be carboxyl, amino or the like, but the preferred reactive groups are hydroxyl such as are found on cellulose. The cellulose may be unmodified as in cotton or paper or regenerated as in rayon or partially esterified as in cellulose acetate, cellulose propionate and especially cellulose nitrate, or partially etherified as in methylcellulose and carboxymethylcellulose.

While the photochemically active intercalator reagent could be directly combined with the solid substrate, advantageously there is a mutual coupler which makes the connection. Suitable reagents include bifunctional compounds such as cyanogen bromide (CNBr), 1,4-butanediol diglycidyl ether, and the like. These are reacted with both the solid substrate and the photochemical reagent simultaneously or first with one and then with the other.

Thereafter, the product is further reacted with the nucleic acid photochemically. The reactions with the coupler and nucleic acid are substantially quantitative so the quantities of the reagents employed depend upon the desired ratio of nucleic acid to solid support. For most purposes, about 0.1 to 1000 mg and preferably about 1 to 100 mg of nucleic acid per gram of solid support will be suitable, although it may be higher or lower, depending upon the molecular weight of the nucleic acid, its sensitivity and the particular test in which it is to be used.

The reaction conditions in each step are generally known per se and any solvents and temperatures can be employed which permit the reactions to proceed without interference, e.g., from about $-10°$ to $100°$ C., preferably about $10°$ to $50°$ C., and most preferably room temperature, employing inert organic solvents such as ether, carbon tetrachloride, THF, and the like.

The photochemically active reagents herein employed preferably react through amino groups. Identifying it as $RNH_2$ and the substrate with pendent OH groups as S, the stepwise reactions are as follows:

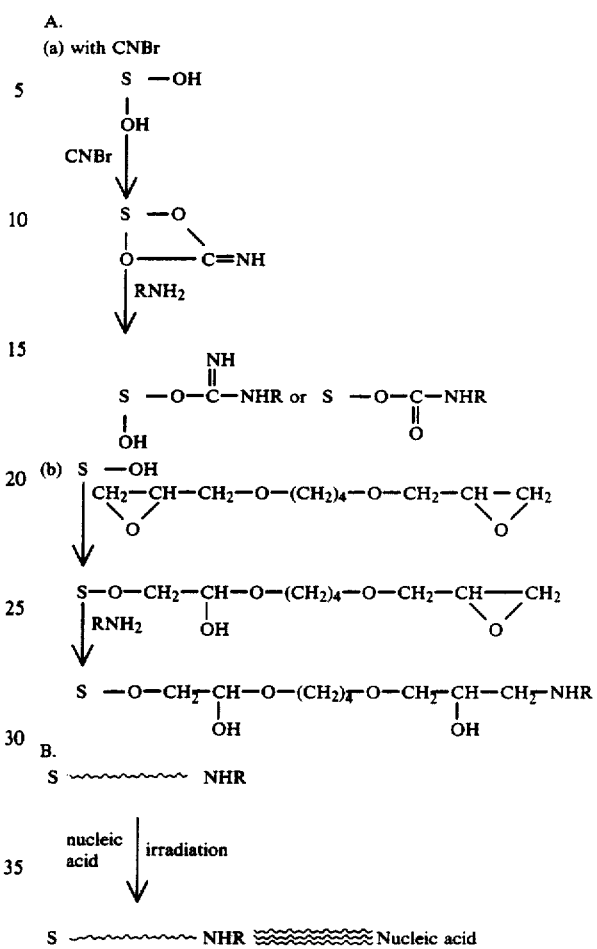

Amino-derivatives of angelicin and psoralen react correspondingly, if not identically.

The particular wavelength of radiation selected will depend upon the particular photoreagent and whether it is desired to bind to a single strand of nucleic acid or to a double strand. If to both strands it can be in a manner and to a degree such that the nucleic acid is no longer denaturable.

The nucleic acid can be RNA or DNA of short (oligonucleotide) or long chain length, as desired, doubly or singly stranded.

Formation of monoadducts is desirable for hybridization experiments. In crosslinks, both DNA strands are covalently linked to psoralen chromophore and hence strand separation prior to hybridization is difficult. If the probe to be hybridized is linked to another non-specific piece of DNA, the non-specific part can be linked either via crosslink or monoadduct formation. In this case, irradiation can be done at any wavelengths between 300–390 nm. Irradiation at 390 nm produces monoadduct; irradiation at 360–300 nm produces both monoadduct and crosslinks.

If angelicin compounds are used, the product will predominantly be monoadduct irrespective of the wavelength of irradiation.

The invention will now be further described with reference to the accompanying examples wherein all parts are by weight unless otherwise expressed.

EXAMPLE

1. Activation of the solid support and coupling of AMT.

The procedure described below has been followed for Sephadex G25 and cellulose, but any hydroxy-containing solid support can be activated by an identical procedure.

(a) Activation with 1,4-butane-diol-diglycidyl ether.

0.5-1 gm solid powder is swollen with water and washed, then 5-10 ml sodium hydroxide solution (0.5M) is added. To this thick suspension, 1 ml 1,4-butanediol-diglycidyl ether is added. The suspension is shaken overnight on a mechanical shaker and then washed with sodium hydroxide (0.5M) solution and 1.0 ml 4'-aminomethyl-4,5',8-trimethyl-psoralen (2 mg/ml) in water is added, followed by enough 1M sodium hydroxide to have a thick suspension. The suspension is then stirred gently for 24 hours at room temperature and excess unreacted residues are quenched with lysine.

The solid is then washed with water followed by the desired aqueous buffer solution for DNA coupling.

(b) For epoxidation of paper the identical procedure is followed with Whatman filter papers type 540, 1 and 541. The filter papers are taken on a watch glass or beaker cover (glass) and turned occasionally by hand. The rest of the procedure is the same as above.

(c) Activation by cyanogen bromide and coupling of AMT. Typical example with cellulose:

0.5 gm cellulose is swollen in 5.0 ml distilled water for one hour. The swollen gel is washed thoroughly with distilled water. Then it is taken in an erlenmeyer flask, ice-cooled distilled water is added to the swollen cellulose and the pH is adjusted between 10.5-11 with 5M sodium hydroxide solution. The flask with its contents is cooled in ice to avoid temperature rise above 15° C. 1 gm of solid cyanogen bromide is added to the cellulose and the solution is stirred for 30 minutes and pH maintained between 10.5-11 by NaOH. The suspension is washed with ice cold distilled water, water is removed by centrifugation and 20 ml ice cold potassium phosphate buffer (10 mM; pH 8) is added. The activated cellulose is kept in brown bottles (in small aliquots) at −20° C.

2-3 ml of swollen, activated gel is taken in a brown bottle and 0.7 ml AMT (2 mg/ml) is added and the mixture is shaken gently in the cold room. Excess activated residues are quenched with lysine. The solid is washed with aqueous buffer for DNA binding.

(d) For papers, similar procedures have been followed with Whatman cellulose filter papers type 540, 1 and 541 quantitative papers. Care should be taken to avoid tearing of the papers.

(e) Parallel experiments with $^3$H labelled aminomethylpsoralen or angelicin are used to estimate labelling efficiency.

2. Coupling of phenanthridium compounds to a solid support and azide formation for photochemical coupling of DNA:

Activation of the solid supports is done by the method described above. As an example, methidium propylamine (R. P. Hertzberg and P. B. Dervan, JACS, 104, 313 (1982)) is coupled to the solid support, using identical buffer conditions as in 1. The isolated methidium containing solid support is then diazotized and azide derivative is made as follows. 1 gm cellulose or (2×5 cm$^2$) of a sheet of activated paper containing methidium chloride is taken in 20 ml water, cooled in ice, 0.2 ml ice cold HCl is added; sodium azide (20 mg solid; 2×) is added. The vessel is cooled in ice and sodium nitrate solid (100 mg) is added. The reaction is allowed to proceed for 30 minutes, solid support is washed with the desired buffer. Coupling of DNA and hybridization are carried out the same way as described for aminomethyl-psoralen. Aminomethyldimethylangelicin can be similarly treated.

3. Photochemical coupling of DNA:

0.5 ml (0.2-0.3 gm gel+buffer) activated solid powder or 0.8 × 1 cm$^2$ activated paper is taken in a 1 cm path length spectrophotometer cuvette. Adenovirus DNA (partially labelled with $^3$H) (concentration 25 μg/ml) in tris EDTA buffer (10 mM tris, 1 mM EDTA, pH 7.5) is added to the cuvette and irradiation is done at a desired wavelength for 30 minutes to two hours depending on the future needs. For AMT, irradiation at 390 nm produces monoadduct whereas at 360-300 nm both monoadduct and crosslinks are formed. By altering the concentration and DNA sequence, crosslink to monoadduct formation can be modulated. After photoirradiation, the solid is washed and the radioactivity of the washings and the solid support is counted in a Beckman 7800 scintillation counter.

Typical Results

| Solid support | % Coupling | DNA Coupled μg |
|---|---|---|
| 0.5 ml or 0.8 × 1 control paper (No DNA) | — | — |
| BDGE treated paper | 80 | 20 |
| Cellulose cellex CNBr activated | 91.5 | 22.5 |
| Cellulose cellex BDGE activated | 93.4 | 22.5 |
| Sephadex G25 CNBr activated | 69.5 | 18.0 |

4. Assay for DNA-DNA hybridization of DNA photochemically coupled to the solid support:

Andenovirus DNA is covalently coupled to the solid support as above and hybridization with $^3$H labelled adenovirus DNA is done following the procedure of Noyes and Stark, Cell, 5, 301-310 (1975).

5. Use of photochemically coupled DNA for sickle cell diagnosis:

AMT coupled DNA can be recovered as free DNA by irradiation at 260 nm. The separation probe (Application Ser. No. 511,063, supra) is coupled to the solid support by the method described above. Then the support with the coupled DNA is mixed with the unknown and the detection probe under hybridization condition—as in 4. The solid support is then tested for the presence of label. If a radioactively labelled detection probe is used, radioactivity is counted.

5a. The product of 4 is irradiated at 260 nm in otherwise the same manner as in 3, whereupon the DNA uncouples from the solid support, entering the solvent medium, viz. aqueous buffer. Then the liquid is assayed for $^3$H.

It will be understood that the specification and examples are illustrative but not limitative of the present invention and that other embodiments within the spirit and scope of the invention will suggest themselves to those skilled in the art.

What is claimed is:

1. A solid support capable of binding a nucleic acid thereto upon suitable irradiation, comprising (a) a solid substrate, (b) a photochemically reactive nucleic acid-binding ligand, and (c) a divalent radical chemically linking the substrate and the nucleic acid-binding ligand.

2. A support according to claim 1, wherein the nucleic acid-binding ligand is an intercalator compound selected from the group consisting of acridine dyes, phenazines, phenothiazines, and quinolines.

3. A support according to claim 1, wherein the substrate (a) in free state has free OH groups through which it is linked by the divalent radical (c).

4. A support according to claim 1, wherein the substrate (a) is cellulose or a cellulose ester.

5. A support according to claim 1, wherein the divalent radical (c) is derived from cyanogen bromide.

6. A support according to claim 1, wherein the divalent radical (c) is derived from 1,4-butanediol-diglycidyl ether.

7. An immobilized nucleic acid probe comprising (a) a nucleic acid, (b) a nucleic acid-binding ligand photochemically linked to the nucleic acid, and (c) a solid substrate chemically linked through a divalent radical to the nucleic acid-binding ligand (b).

8. An immobilized probe according to claim 7, wherein the nucleic acid-binding ligand is an intercalator compound selected from the group consisting of acridine dyes, phenazines, phenothiazines, and quinolines.

9. An immobilized probe according to claim 7, wherein the substrate (c) in free state has free OH groups through which it is linked by the divalent radical.

10. An immobilized probe according to claim 7, wherein the substrate (c) is cellulose or a cellulose ester.

11. An immobilized probe according to claim 7, wherein the divalent radical is derived from cyanogen bromide.

12. An immobilized probe according to claim 7, wherein the divalent radical is derived from 1,4-butanediol-diglycidyl ether.

* * * * *

UNITED STATES PATENT AND TRADEMARK OFFICE
CERTIFICATE OF CORRECTION

PATENT NO. : 4,713,326
DATED : Dec. 15, 1987
INVENTOR(S) : Dattagupta et al.

It is certified that error appears in the above-identified patent and that said Letters Patent is hereby corrected as shown below:

Col. 4, under last formula    Insert --methidium monoazide--
Col. 5, under formula    Insert --methidium diazide--

Signed and Sealed this

Fifth Day of July, 1988

Attest:

Attesting Officer

DONALD J. QUIGG

Commissioner of Patents and Trademarks